(12) United States Patent
Lin et al.

(10) Patent No.: US 7,259,265 B2
(45) Date of Patent: Aug. 21, 2007

(54) COUMARIN COMPOUNDS AND METHOD FOR PREPARING AND USING THE SAME

(75) Inventors: Guoqiang Lin, Shanghai (CN); Jianguang Lei, Shanghai (CN); Minghua Xu, Shanghai (CN); Jin Ren, Shanghai (CN)

(73) Assignee: Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 11/273,372

(22) Filed: Nov. 15, 2005

(65) Prior Publication Data

US 2006/0063806 A1 Mar. 23, 2006

Related U.S. Application Data

(63) Continuation-in-part of application No. PCT/CN2004/000491, filed on May 17, 2004.

(30) Foreign Application Priority Data

May 15, 2003 (CN) .................. 03 1 16952

(51) Int. Cl.
*C07D 311/02* (2006.01)
*C07D 311/00* (2006.01)
(52) U.S. Cl. ................. 549/283; 549/289; 549/290
(58) Field of Classification Search ............. 549/290, 549/289, 283
See application file for complete search history.

(56) References Cited

U.S. PATENT DOCUMENTS

| 4,083,857 A | 4/1978 | Townend et al. |
| 5,554,611 A | 9/1996 | Schonafinger et al. |

FOREIGN PATENT DOCUMENTS

| JP | 02-191269 | * 7/1990 |
| JP | 2876129 | 1/1999 |
| WO | WO9804572 | 2/1998 |
| WO | WO9825608 | 6/1998 |

OTHER PUBLICATIONS

Pillon et al., Bull. Soc. Chim., "Derivatives of flavones. III. Synthesis of polyhydroxy flavones", 1954, pp. 9-25.*
Gogte et al., Physical Sciences, Mathematics, Biological Sciences and Medicine, "Elimination of Acetic acid during decarboxylation of organic acids part III. A new synthesis of 4-aryl-coumarins from B, B'-diarylglutaromonolactonic acids", 1959, vol. 27, pp. 6-13.*
Saxena et al., Proceedings of the National Academy of Sciences, India, Section A: Physical Sciences, "A new 4-phenylcoumarin 'Sisafolin' from *Dalbergia Latifolia*", 1970, vol. 40(pt. 2), pp. 165-169.*
Tickle et al., Journal of the Chemical Society, Perkin Transactions 1: Organic and Bio-organic Chemistry, "Intraction of Gringnard reagents with coumarins. I. Novel 1,40addition", 1974, vol. 5, pp. 569-574.*
Chawla et la., Bulletin de la Societe Chimique de France, "New Phenolic coponents from *Dalbergia volubilis*", 1989, vol. 1, pp. 82-87.*
Zou et al., Yaoxue Xuebao, "Structure determination of inflacoumarin A from *Glycyrrhiza inflata*", 1994, vol. 29, pp. 397-399.*
Zou et al., Journal of Chinese Pharmaceutical Sciences, "Constituents from *Glycyrrhiza inflata* and antioxidant activities of phenols from the roots of *Glycyrrhiza*", 1994, vol. 3, p. 90.*
Yianbin et al., Bopuxue Zazhi, "NMR study of inflacoumarin A", 1994, vol. 11, pp. 399-403.*
Wu et al., Tetrahedron Letters, "Palladium-catalyyzed cross-coupling reactions of 4-tosyloxycoumarin and arylboronic acids: synthesis of 4-arylcoumarin compounds", 2002, vol. 43, pp. 4395-4397.*

(Continued)

*Primary Examiner*—Margaret D. Seaman
*Assistant Examiner*—Niloofar Rahmani
(74) *Attorney, Agent, or Firm*—Manni Li; Perkins Coie LLP

(57) ABSTRACT

4-Substituted coumarin compounds having the general formula of

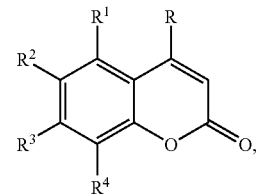

where R is H, CHO, $OCH_3$, X, $NO_2$, an alkyl having $C_{1-10}$, —$OCH_2O$—, an aryl being mono- or poly-substituted with CN or $COOCH_3$ with the aryl being a phenyl, naphthyl, or azaryl, or a coumarin group

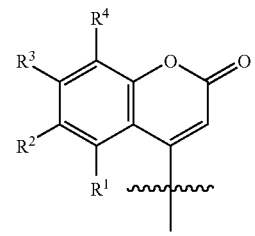

that is substituted with $R^1$, $R^2$, $R^3$, $R^4$, with $R^1$, $R^2$, $R^3$, and $R^4$ being H, an alkyl having $C_{1-10}$, X, $NO_2$, CN, $OCH_3$, $COOCH_3$ or $OR^5$, $R^5$ being H or an alkyl having $C_{1-10}$, and X being a halogen.

3 Claims, No Drawings

OTHER PUBLICATIONS

Garazd et al., Chemistry of Natural Compounds (Translation of Khimiya Prirodnykh Soedinenii), Modified Coumarins. 8. Synthesis of substituted 5-(4-Methoxyphenyl)-7H-furo[3,2-g]chromen-7-ones, 2002, vol. 38, pp. 539-548.*

Lei Jianguang et al., The first total systhesis of 4, 4-bisisofraxidin, Chinese J. Chem., (2002), 20, 1263-1267, the whole document.

Pharkphoom P. et al.; "a new biscoumarin from impatiens balsamina root cultures", Planta Medica, (1998), 64, 774-775, compound 1.

Paradkar M. V. et al.; "a facile synthesis of new [4, 4-bi-2H-1-benzopyran]-2, 2-diones", Synthetic Communications, (1988), 18(6), 589-596, 1, compound 3a-c.

Zhang yanying et al., "a study on the synthesis and spectra characteristics of coumarins", Dyestuffs and Coloration, (2002), 40 (2), 68-70, the whole document.

Min-liang Yao et al., "a novel and convenient method to 4-substituted coumarins", Heteroatom Chem., (2000), 11(6), 380-382, table 1.

Laurent Schio et al., "tosylates in palladium-catalysed coupling reactions. Application to synthesis of arylcoumarin inhibitors of gyrase B", Tetrahedron Lett., (2000), 41, 1543-1547, table 1.

Jayati et al., "Palladium in organic synthesis: Part IV palladium (0) catalyzed arylation of coumarin", Indian J. Chem., (1996), 35B, 588-589, table 1.

Bose et al., "synthesis of 4-phenylcoumarins", Indian J. Chem., (1990), 29B , 422-424, table 1.

Dervilla, "a new approach to neoflavonoid synthesis", J. Chem. Soc. Perkin Trans., (1990), 1, 2851-2852, table 1.

Zhang yanying et al., "current development in synthetic methods for arylcoumarins", Dyestuffs and Coloration, (2002), 40 (1), 39-41, the whole document.

Mohammad e tal., "biomimetic synthesis of some novel coumarin dimers", Tetrahedron, (1996), 52(11), 3991-3996.

Johannes, "synthesis of the natural coumarins (E)-suberenol, cyclobisuberodiene and two other related new coumarins", J. Reisch, Natural Products Chem., (1990), 139, 931-933.

Soroush et al., "synthesis and antifungal activity of coumarins and angular furanocoumarins", Bioorg. Med. Chem., (1999), 7, 1933-1940.

Hao xiaojiang et al., "the chemical constituents of boenninghausenia sessilicarpa", Acta Botanica Yunnanica, (1994), 16(3), 310-312.

Zhao yajun et al., "a reverse friedel-crafts reaction and the synthesis of enzo[h]coumarin", Acta Scientiarum Naturalium Universitatis Perkinensis, (1994), 30 (4), 421-424.

* cited by examiner

COUMARIN COMPOUNDS AND METHOD FOR PREPARING AND USING THE SAME

FIELD OF THE INVENTION

The present invention relates to coumarin compounds and method for preparing and using the same. The coumarin compounds of the present invention have significant antifungal activities and may be used for preparing medicament for treating fungal infection such as whitlow and ringworm of the nails.

BACKGROUND OF THE INVENTION

Fungal infection has been a common disease which greatly affects health. The incidence of fungal infection in deep tissue and mortality caused therefrom has increased dramatically in the recent decades due to the extensive application of clinical wide-spectrum antibiotics, hormones, anti-tumor drugs, and immunosuppressants, development of large scale organ transplantation operation, spread of AIDS, and even SARS in first half of the year 2003. Highly effective antifungal drugs with low toxicity have been in urgent and great demand. However, there are only a limited number of known clinically available antifungal reagents that can be chosen from, including amphoterlcin B, Ketoconazole, Fluoroconazole, and Itraconazole. In the recent years, research and development of antifungal drugs have been focused on azoles compounds. Multinational pharmaceutical companies have developed these medicaments in clinical use. Voriconazole developed by Pfizer Inc. has been on the international market since the year 2002; Posaconazole developed by Schering-Plough is known to be coming into the market soon. Despite of certain advantages of these newly developed antifungal drugs, they have disadvantages including high toxicity, ineffective towards some fungi, and low bioavailability, thus, they are not able to fully meet the needs of the patients. There still exists the great and urgent demand for developing an effective antifungal drug with high bioavailability and low toxicity.

Coumarin is a lactone of o-hydroxycassia acid which can be found in the plant world of the family of *Umbelliferae, Leguminosae, Rueae, Compositae, Saxifragaceae,* and *Thymelaeaceae* as well as in the metabolites of microorganisms, while coumarin can not be found at all in the animal world. Coumarin can be found in all parts of plants in the descending order of richness as fruits>roots and fibrous roots>stems>leaves. About 800 coumarin compounds have been identified since the year 1980.

Furanocoumarin has been used for ages in traditional medicine. The Indian myth bible "Athara Veda" describes the treatment of leukoderma by a paste medicament prepared from the refinement of *Psoralea corylifolia* tree; ancient Egyptians used *Ammi majus* to cure vitiligo. In 1838, Kalbrunner was the first to separate furanocoumarin and 5-methoxypsoralen from bergamot (Scott, B. R.; Pathak, M. A.; Mohn, G. R. *Mutat. Res.*, 1976, 39, 29.).

Coumarin compounds have extensive bioactivities. For examples, coumarin compounds can be used as anticoagulant, estrogenic, they have anti-dermal photosensitizing activity, they are antibiotics, vasodilators, molluscacides, anthelmintics, sedatives and hypnotics, analgesics and having hypothermal activity (Soine, T. O. J. Pharm. Sci., 1964, 53, 231; Edelson, R. L. Sci. Am., 1988, August, 68; Dini, A.; Ramundo, E.; Saturnino, P.; Stagno, d'Alcontres, I. Boll. Soc. Ital. Biol. Sper., 1992, Univ. Lodz). Coumarin compounds have been known as the pharmaceutical promiscuity for the extensive bioactivities. (Hoult, J. R.; Paya, M. Gen. Pharmacol., 1996, 27, 713) Coumarin compounds that have significant physiological effects include: aflatoxin having acute hepatotoxicity and carcinogenicity, dicoumarol having anticoagulation (Rocha, L.; Marston, A.; Kaplan, M.; Stoeckli-Evans, H.; Thull, U.; Testa, B.; Hostettmann, K. Phytochem, 1994, 36, 1381); novobiocin and coumermycin A1 having antibiotic activity; some linear furanocoumarins having photosensitivity at the cellular level, which has caused vast interested from biochemists and has been used for assisting in crosslinking of DNA fragments. Structures and physiological activities for some compounds are listed below. (Stud. Nat. Prod. Chem., 2000, 33 (Bioactive Natural Products(Part D), 350.)

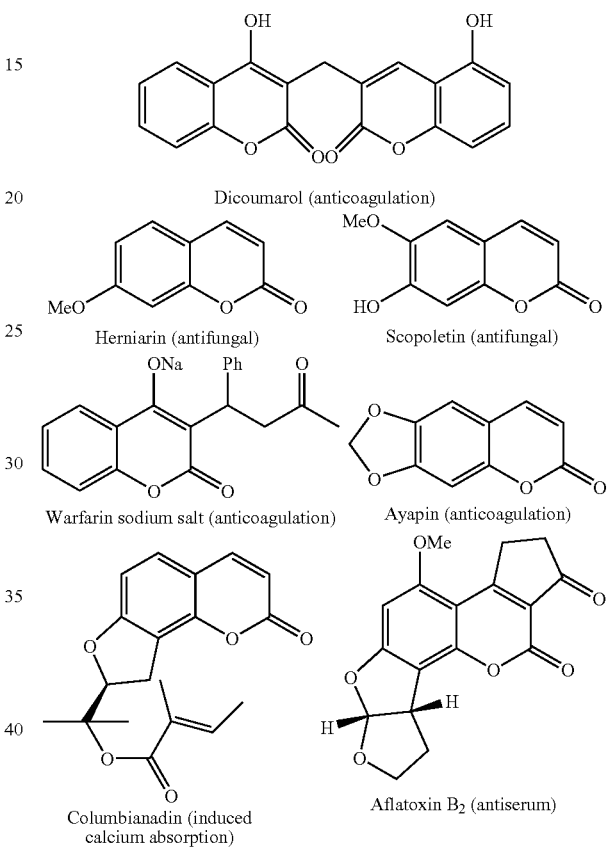

Due to their wide-ranging availability in plants and excellent bioactivity, many coumarin compounds have been used for preparing medicaments, which has invoked great interest in chemists, pharmaceutical industry researchers, and biologists.

SUMMARY OF THE INVENTION

It is an object of the present invention to provide novel coumarin compounds having the following general formula:

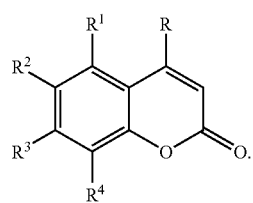

It is an another object of the present invention to provide a method for preparing the novel coumarin compounds of the present invention. The coumarin compounds of the present invention may be prepared by reacting coumarin sulfonate substituted with $R^1$, $R^2$, $R^3$, and $R^4$ with aryl halide, or halogenated coumarin compounds substituted with $R^1$, $R^2$, $R^3$, and $R^4$, or another halogenated coumarin sulfonate substituted with $R^1$, $R^2$, $R^3$, and $R^4$ in the presence of a catalyst which is a bivalent or non-valent Palladium or Nickel compound and a phosphine ligand, an organic solvent and Zn at a temperature of 60 to 100° C. and reaction time of 0.5 to 20 hours.

It is yet another object of the present invention to provide a method of using the novel coumarin compounds of the present invention for preparing medicaments having high antifungal activities. The antifungal drugs can be used for treating fungal infection such as whitlow and ringworm of nails. The present invention provides a method for treating diseases caused by fungal infection by administering an effective amount of 4-substituted coumarin compounds to a subject. the 4-substituted coumarin compounds have a formula of

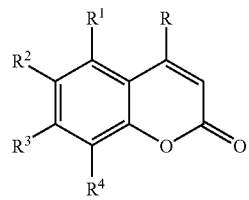

where R is H, CHO, $OCH_3$, X, $NO_2$, an alkyl having $C_{1-10}$, —$OCH_2O$—, an aryl being mono- or poly-substituted with CN or $COOCH_3$ with the aryl being a phenyl, naphthyl, or azaryl, or a coumarin group

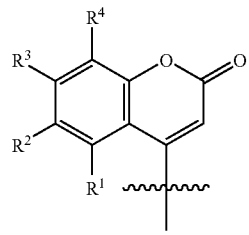

that is substituted with $R^1$, $R^2$, $R^3$, $R^4$, with $R^1$, $R^2$, $R^3$, and $R^4$ being H, an alkyl having $C_{1-10}$, X, $NO_2$, CN, $OCH_3$, $COOCH_3$ or $OR^5$, $R^5$ being H or an alkyl having $C_{1-10}$, and X being a halogen.

The 4-substituted coumarin compound and a pharmaceutically acceptable carrier are mixed for making a medicament for treating the disease caused by fungal infection. The pharmaceutical acceptable carrier is within the knowledge of one of ordinary skill in the art. The 4-substituted coumarin compound has no toxicity effects on the subject. Especially, the 4-substituted coumarin compound has no liver toxicity or acute toxicity on the subject. The 4-substituted coumarin may be a 4,4'-biisofraxidin. Particularly, the 4,4'-biisofraxidin has a formula of

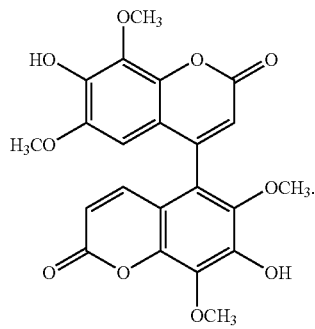

DETAILED DESCRIPTION OF THE INVENTION

The novel coumarin compounds of the present invention have the following general formula:

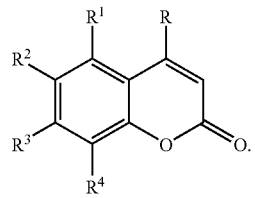

In the formula, R may be H, CHO, $OCH_3$, X, $NO_2$, an alkyl having $C_{1-10}$, —$OCH_2O$—, an aryl being mono- or poly-substituted with CN or $COOCH_3$ with the aryl being a phenyl, naphthyl, or azaryl, or a coumarin group

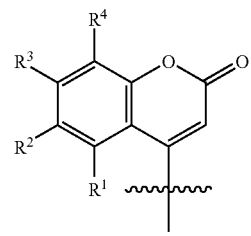

that is substituted with $R^1$, $R^2$, $R^3$, $R^4$, with $R^1$, $R^2$, $R^3$, and $R^4$ being H, an alkyl having $C_{1-10}$, X, $NO_2$, CN, $OCH_3$, $COOCH_3$ or $OR^5$, $R^5$ being H or a $C_{1-10}$ alkyl, and X being a halogen.

On the other hand, the following coumarin compounds are expressly excluded from the novel coumarin compounds of the present invention:

a) If R is an aryl, it cannot be the following compounds:

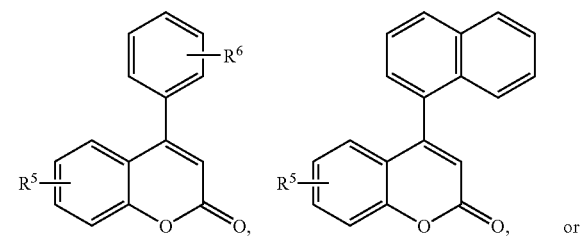

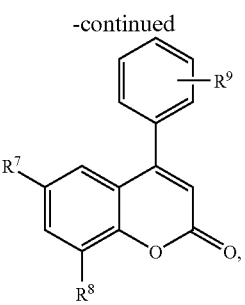

$R^5$ is H, OH, OCH$_3$, an alkyl having C$_{1-10}$ or a halogen; $R^6$ is H, CH$_3$, CH$_3$O or a halogen; $R^7$ is CH$_3$O or OH; $R^8$ is CH$_3$O or OH; $R^9$ is H, CH$_3$, OH or —OCH$_2$O—;

b) If R is a coumarin group, the following compound is excluded:

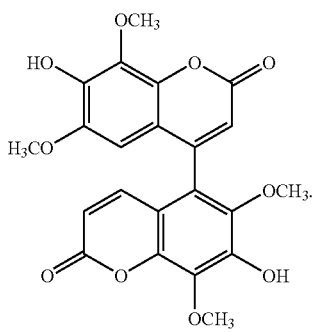

Examples of the novel coumarin compounds of the present invention include

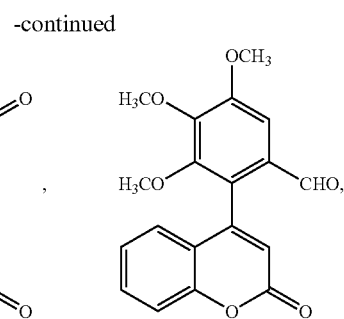

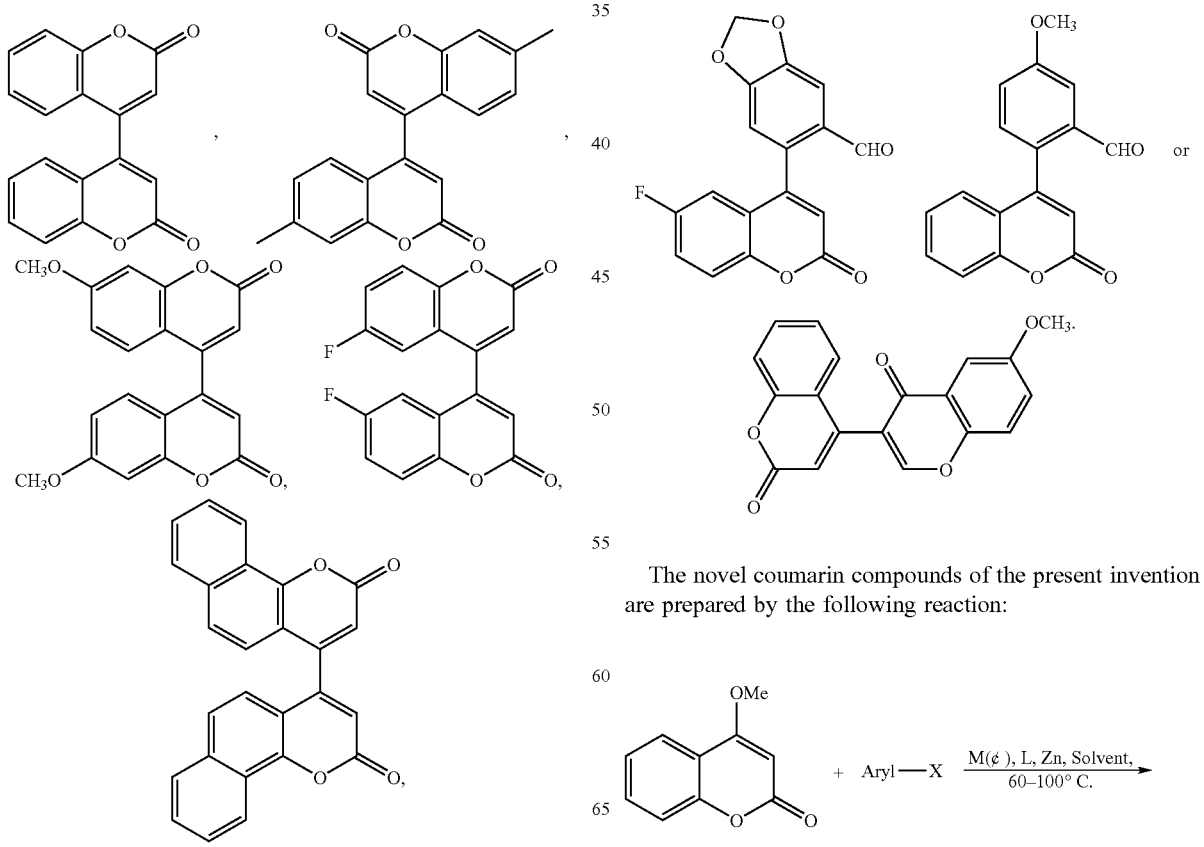

The novel coumarin compounds of the present invention are prepared by the following reaction:

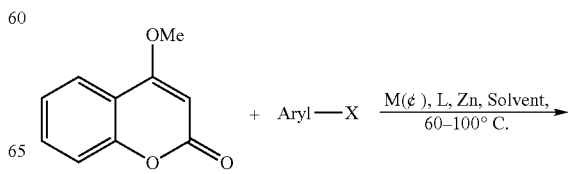

-continued

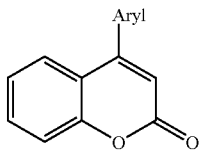

In the synthetic reaction for making the coumarin compounds of the present invention, a coumarin sulfonate substituted with $R^1$, $R^2$, $R^3$, and $R^4$ serves as a substrate and is reacted with a reactant which is an aryl halide, or a halogenated coumarin compound substituted with $R^1$, $R^2$, $R^3$, and $R^4$, or another halogenated coumarin sulfonate substituted with $R^1$, $R^2$, $R^3$, and $R^4$. The reactant coumarin compound has the following general formula of

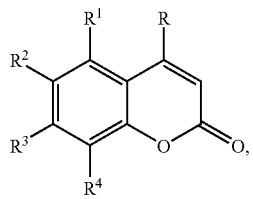

with $R^1$, $R^2$, $R^3$, and $R^4$ each being H, an alkyl having $C_{1-10}$, X, $NO_2$, CN, $OCH_3$, $COOCH_3$ or $OR^5$, $R^5$ being H or a $C_{1-10}$ alkyl, and X being a halogen. The halogen is iodine, bromine, or chlorine; the aryl is aryl halide, naphthyl halide, azaryl halide substituted with H, CHO, $OCH_3$, X, $NO_2$, $C_{1-10}$ alkyl, CN, or $COOCH_3$.

A bivalent or non-valent Palladium or Nickel compound and phosphine ligand serves as the catalyst. The reaction is carried out in an organic solvent and in the presence of Zinc. The reaction temperature is between 60 to 100° C. The reaction time is between 0.5 to 20 hours. The molar ratio of the substrate, bivalent or non-valent Pd or Ni compound, phosphine ligand, Zn, and the reactant is 1:(0.05~1):(0.05~1):(1~5):(1~10).

In other words, the substrate for the synthetic reaction in the present invention may not only react with an aryl halide or a halogenated coumarin compound substituted with $R^1$, $R^2$, $R^3$, and $R^4$, but also undergo self-coupling reaction.

In above-mentioned reaction, the bivalent or non-valent Pd or Ni compound may be di(triphenyl phosphine)palladium dichloride ($PaCl_2(PPh_3)_2$), di(triphenyl phosphine) nickel dichloride ($NiCl_2(PPh_3)_2$), tetra(triphenyl phosphine) palladium ($PPh_3)_4$, or tetra(triphenyl phosphine) nickel (Ni $(PPh_3)_4$. The phosphine ligand may be 1,2-bi(biphenyl phosphine)ethane, 1,3- bi(biphenyl phosphine)propane, 1,4-bi(biphenyl phosphine)butane, 1,1'- bi(biphenyl phosphine) ferrocene, 2,2'- bi(biphenyl phosphine)binaphthalene (BINAP), or triphenyl phosphine, with X being a halogen including iodine, bromine, or chlorine. The organic solvent may be benzene, toluene, petroleum ether, carbon tetrachloride, or tetrahydrofuran.

The method of the invention not only is simple and convenient to carry out, but also results in coumarin compounds with excellent antifungal activity. The coumarin compounds of the present invention may be used to prepare medicaments to cure fungal infection such as whitlow and ringworm of nails. The coumarin compounds of the present invention may be mixed with a pharmaceutically acceptable carrier for making a medicament for treating the disease caused by fungal infection. An effective dosage of the coumarin compound may be administered to the subject. The pharmaceutically acceptable carrier is known to one of ordinary skill in the art.

The present invention provides novel coumarin compounds of the general formula as described, which can be used to prepare some medicaments to cure fungal infection. The medicaments prepared from the coumarin compounds of the present invention are highly effective against fungal infection and have low toxicity which would allow wide application clinically.

The present invention is explained in details by the following examples. The examples are meant only for illustrating purpose and do not limit the scope of the invention which is defined in claims.

EXAMPLE 1

Preparation of 4-(4,5,6-trimethoxy-2-benzaldehyde) coumarin (1)

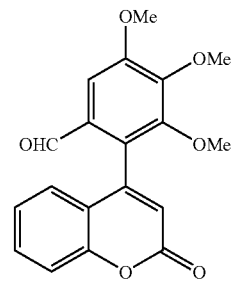

The substrate 4-coumarin methane (1~100 mmol), $NiCl_2$ $(PPh_3)_2$ (0.2~20 mmol), $PPh_3$ (0.4~40 mmol), and activated Zn powder (3~300 mmol) were added to a dry 10~1000 ml reactor, and 4~400 ml anhydrous toluene was added to the reactor. The mixture was heated to 90° C. in oil bath, and 3,4,5-trimethoxy-2-iodobenzaldehyde (1~100 mmol) that had been dissolved in 4~400 ml anhydrous toluene was added slowly and dropwise through an automatic syringe. The mixture was stirred for 0.5~20 hours, and then, allowed to cool down to room temperature naturally. Then, 5% hydrochloric acid (4~400 ml) and dichloromethane (4~400 ml) were added to the reactor, and the mixture was stirred for 1 hour. After the reaction mixture became clear, the water layer (3×10~1000 ml) was extracted with $CH_2Cl_2$. The organic layer (10~1000 ml) was washed successively with saturated aqueous sodium hydrogen carbonate (aq $NaHCO_3$) and saturated aqueous sodium chloride (brine), and after the layer was dried for 2 hours over anhydrous sodium sulfate, the residue obtained by filtration and concentration was purified by column chromatography to give the title compound (1). The yield was 71% and the product was characterized by the following:

$^1$H NMR (300 MHz, $CDCl_3$) δ: 9.70(s, CHO, 1H), 7.56(s, Ph, 1H), 7.45-7.03(m, Ph, 4H), 6.41(s, CH, 1H), 4.02(s, OMe, 3H), 3.99(s, OMe, 3H), 3.73(s, OMe, 3H);

EI-MS (m/z, %): 341($M^+$+1, 100), 340($M^+$, 91.40), 325 (76.86), 297(47.70), 282(23.64), 281(34.42), 237(22.72), 155(17.46);

IR (KBr, $cm^{-1}$): 3007, 2987, 2941, 1726, 1677, 1603, 1587, 1562, 1484, 1365, 1331;

HRMS. $C_{19}H_{16}O_6$, calculated value: 340.09469; measured value: 340.09561.

EXAMPLE 2

Preparation of 4-(3-methoxy phenyl) coumarin (2)

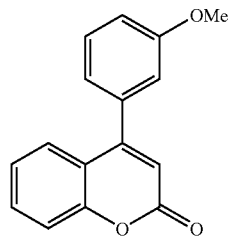

The substrate 4-coumarin methane sulfonate (1~100 mmol), $NiCl_2(PPh_3)_2$ (0.2~20 mmol), $PPh_3$ (0.4~40 mmol), and activated Zn powder (3~300 mmol) were added to a dry 10~1000 ml reactor, and then added 4~400 ml anhydrous toluene. The mixture was heated to 90° C. in oil bath, and 3-methoxy-2-iodobenzene (1~100 mmol) that had been dissolved in 4~400 ml anhydrous toluene was added slowly, and the mixture was stirred for 0.5~20 hours. After then, it was cooled down to room temperature naturally, and 5% hydrochloric acid (4~400 ml) and dichloromethane ($CH_2Cl_2$) (4~400 ml) were added to the reactor, and the mixture was stirred for 1 hour. After the reaction mixture became clear, the water layer (3×10~1000 ml) was extracted with $CH_2Cl_2$. The organic layer (10~1000 ml) was washed successively with saturated aqueous sodium hydrogen carbonate (aq $NaHCO_3$) and saturated aqueous sodium chloride (brine), and after the layer was dried for 2 hours over anhydrous sodium sulfate, the residue obtained by filtration and concentration was purified by column chromatography to give the title compound (2). The yield was 70% and the product was characterized by $^1H$ NMR (300 MHz, $CDCl_3$) δ: 7.56-7.05(m, Ph, 6H), 6.99(s, Ph, 1H), 6.40(s, CH, 1H), 3.87(s, OMe, 3H) ppm;

EI-MS (m/z, %): 263($M^+$+1, 19.70), 262($M^+$, 100), 261 ($M^+$-1, 20.31), 205(9.38), 184(13.98), 183(64.62), 108(22.78), 107(12.53);

IR (KBr, $cm^{-1}$): 3068, 2846, 1755, 1720, 1596, 1583, 1558, 1470, 1430, 875, 803, 779, 767, 752, 700;

HRMS. $C_{16}H_{12}O_3$, calculated value: 252.07814; measured value: 252.07507.

The compounds from Example 3 to Example 9 were prepared in the same manner as Example 1 and 2. The yield and the physical properties data are described below.

EXAMPLE 3

Preparation of 4-(4,6-dimethoxy-2-benzaldehyde) coumarin (3)

The yield was 67%.

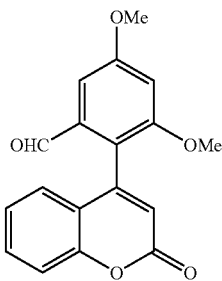

$^1H$ NMR (300 MHz, $CDCl_3$) δ: 9.80(s, CHO, 1H), 7.23-7.03(m, Ph, 3H), 7.01(s, Ph, J=6.6 Hz, 1H), 6.83(s, Ph, 1H), 6.50(s, Ph, 1H), 6.37(s, CH, 1H), 3.88(s, OMe, 3H), 3.76(s, OMe, 3H) ppm;

EI-MS (m/z, %): 311($M^+$+1, 20.33), 310($M^+$, 100), 282 (32.64), 281(23.59), 267(19.94), 262(23.04), 57(24.13), 43(19.92);

IR (KBr, $cm^{-1}$): 3091, 2874, 1729, 1689, 1600, 1564, 1449, 1349, 1361, 1326, 1290;

HRMS. $C_{18}H_{14}O_5$, calculated value: C, 69.67; H, 4.55; measured value: C, 69.58; H, 4.37.

EXAMPLE 4

Preparation of 4-(5,6-dimethoxy-2-benzaldehyde) coumarin (4)

The yield was 72%.

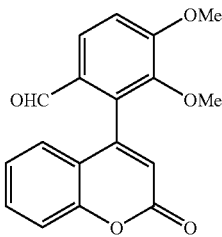

$^1H$ NMR (300 MHz, $CDCl_3$) δ: 9.69(s, CHO, 1H), 7.86(Ph, 1H), 7.54(Ph, 1H), 7.45(Ph, 1H), 7.22-7.16(Ph, 2H), 7.01(Ph, 1H), 6.40(s, CH, 1H), 4.05(s, OMe, 3H), 3.70(s, OMe, 3H) ppm;

EI-MS (m/z, %): 310($M^+$, 70.50), 296(19.68), 295(100), 267(46.51), 252(29.37), 251(34.84), 236(21.91), 139(27.83);

IR (KBr, $cm^{-1}$): 3088, 2947, 2837, 2733, 1729, 1695, 1683, 1604, 1584, 1566;

HRMS. $C_{18}H_{14}O_5$, calculated value: C, 69.67; H, 4.55; measured value: C, 69.86; H, 4.57.

EXAMPLE 5

Preparation of the Compound (5)

The yield was 83%.

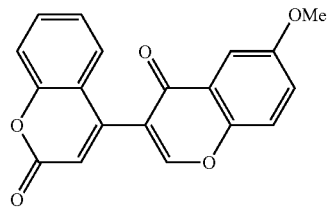

¹H NMR (300 MHz, CDCl₃) δ: 8.08(d, CH, J=2.2 Hz, 1H), 7.64(s, Ph, 1H), 7.54(d, Ph, J=7.5 Hz, 1H), 7.51(d, Ph, J=7.5 Hz, 1H), 7.42-7.21(m, Ph, 4H), 6.45(d, CH, J=2.1 Hz, 1H), 3.93(s, OMe, 3H) ppm;

¹³C NMR(300 MHz, CDCl₃) δ: 175.12, 160.67, 157.84, 154.08, 153.90, 151.45, 148.05, 132.41, 127.02, 124.91, 124.52, 120.90, 120.03, 118.95, 117.70, 117.45, 105.45, 56.28 ppm;

EI-MS (m/z, %): 320(M⁺, 4.26), 292(10.00), 277(34.89), 262(92.13), 183(69.87), 105(100), 71(49.36), 69(40.64);

IR (KBr, cm⁻¹): 3078, 2963, 1720, 1649, 1610, 1488, 1446, 1334, 1271;

HRMS. $C_{19}H_{12}O_5$, calculated value: 320.06848; measured value: 320.07339.

EXAMPLE 6

Preparation of 4-(2-naphthaldehyde) coumarin (6)

The yield was 63%.

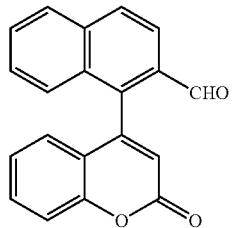

¹H NMR (300 MHz, CDCl₃) δ: 10.06(s, CHO, 1H), 8.63-6.82(m, Ph, 10H), 6.56(s, CH, 1H) ppm;

¹³C NMR(300 MHz, CDCl₃) δ: 190.09, 159.34, 153.34, 150.99, 135.78, 132.49, 130.55, 129.35, 128.43, 127.78, 126.71, 126.15, 124.63, 124.17, 122.44, 120.13, 118.28, 117.06, 116.50, 116.32 ppm;

EI-MS (m/z, %): 300(M⁺, 63.03), 271(30.50), 215(29.10), 118(100), 90(43.25), 89(45.81), 63(27.80), 46(92.08);

IR (KBr, cm⁻¹): 3068, 2855, 1728, 1687, 1606, 1562, 1452;

HRMS. $C_{20}H_{12}O_3$. calculated value: 300,08064; measured value: 300.08357.

EXAMPLE 7

Preparation of 4-(3-N-naphthyl) coumarin (7)

The yield was 30%.

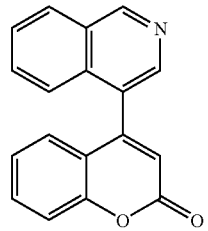

¹H NMR (300 MHz, CDCl₃) δ: 9.42(s, NCH, 1H), 8.13(d, Ph, J=8.2 Hz, 1H), 7.73-7.46(m, Ph, 5H), 7.13-7.01(m, Ph, 2H), 6.55(s, CH, 1H) ppm;

¹³C NMR(300 MHz, CDCl₃) δ:160.50, 154.00, 132.63, 132.24, 132.07, 131.77, 128.67, 128.60, 128.54, 128.49, 128.47, 128.45, 127.26, 124.70, 124.69, 124.51, 117.90, 117.58 ppm;

EI-MS (m/z, %): 274(M⁺,+1,23.33), 273(M⁺, 84.23), 272(M⁺−, 100), 256(49.31), 245(22.69), 244(26.37), 216(31.90), 189(28.37);

IR (KBr, cm⁻¹): 2925, 1752, 1723, 1605, 1560, 1501, 1448, 1360, 757;

HRMS. $C_{18}H_{11}NO_2$: calculated value 273,07900; measured value: 273.08120.

EXAMPLE 8

Preparation of 6-methyl-4-(4-methoxy-2-benzaldehyde) coumarin (8)

The yield was 85%.

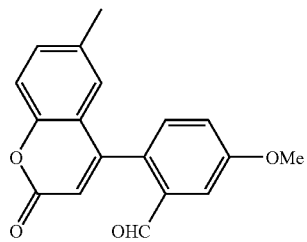

¹H NMR (300 MHz, CDCl₃) δ: 9.82(s, CHO, 1H), 7.58(s, Ph, 1H), 7.32-7.29(m, Ph, 4H), 6.81(s, Ph, 1H), 6.33(s, CH, 1H), 3.94(s, OMe, 3H), 2.26(s, CH₃, 3H) ppm;

EI-MS (m/z, %): 294(M⁺, 9.09), 268(25.37), 256(20.23), 240(21.80), 225(33.97), 199(100), 212(19.84), 105(51.00);

IR (KBr, cm⁻¹): 3442, 2927, 2850, 1726, 1606, 1572, 1487, 1423, 1280, 1251;

HRMS. $C_{18}H_{14}O_4$: calculated value 294.08921; measured value: 294.08517.

EXAMPLE 9

Preparation of the Compound (9)

The yield was 90%.

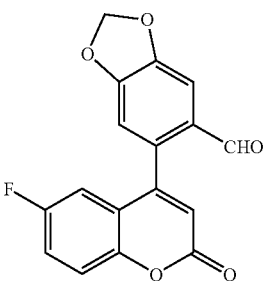

¹H NMR (300 MHz, CDCl₃) δ: 9.70(s, CHO, 1H), 7.54-7.30(m, Ph, 5H), 6.80(s, CH, 1H), 6.39(d, CH₂, J=15 Hz, 2H) ppm;

EI-MS (m/z, %): 312(M⁺, 70.62), 284(83.77), 283(26.33), 270(28.03), 269(100), 256(44.59), 255(20.62), 170(24.33);

IR (KBr, cm⁻¹): 3075, 2913, 2861, 1725, 1682, 1610, 1571, 1504, 1482, 1440, 1369, 1268, 1253;

HRMS. $C_{18}H_{11}FO_4$. calculated value: 312.04340; measured value: 312.03852.

EXAMPLE 10

Preparation of 4,4'-dicoumarin (10)

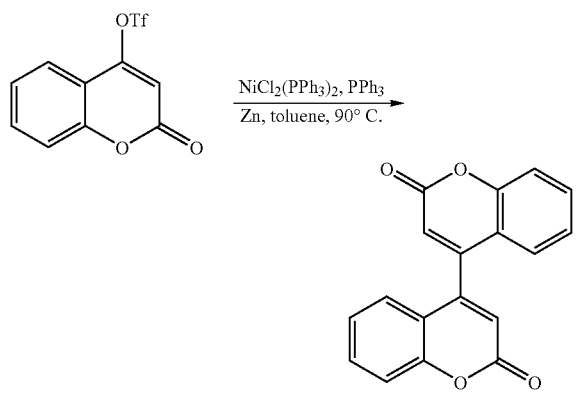

0.5 mmol Substrate, 0.1 mmol NiCl₂(PPh₃)₂, 0.2 mmol PPh₃, 1.5 mmol activated Zn powder, and 3 ml anhydrous toluene were added to a dry 10 ml reactor under high pure argon atmosphere and no oxygen existing. The mixture was heated to 90° C. in oil bath while stirring, and the reaction was tracked. When the reaction was over, it was cooled down to room temperature, and 5% hydrochloric acid (3 ml) and CH₂Cl₂ (3 ml) were added to the reactor, and the mixture was stirred violently. After the reaction mixture became clear, the water layer was extracted with CH₂Cl₂. The organic layer (10~1000 ml) was washed successively with saturated aqueous sodium hydrogen carbonate (aq NaHCO₃) and saturated aqueous sodium chloride (brine), and after the layer was dried for 2 hours over anhydrous sodium sulfate, the residue obtained by filtration and concentration was purified by column chromatography on silica gel (300-400 mesh) to give the title compound (10). The product was characterized by:

¹H NMR (300 MHz, CDCl₃) δ: 7.64(d, Ph, J=9.0 Hz, 1H), 7.48(d, Ph, J=9.0 Hz, 1H), 7.22(m, Ph, 1H), 6.50(s, CH, 1H) ppm;

EI-MS (m/z, %): 290(M⁺, 38.52), 263(23.14), 262(100), 245(44.28), 234(31.48), 218(24.63), 205(37.60), 176(23.22);

IR (KBr, cm⁻¹): 1973, 1854, 1720, 1604, 1560, 1487, 1376, 1357;

HRMS. $C_{18}H_{10}O_4$: calculated value 290.05791. measured value: 290.05670.

The compounds from Example 11 to Example 14 were prepared in the same manner as the method of Example 10. The yield and the physical properties data are described below.

EXAMPLE 11

Preparation of 4,4'-di(7-methyl) coumarin (11)

The yield was 38%.

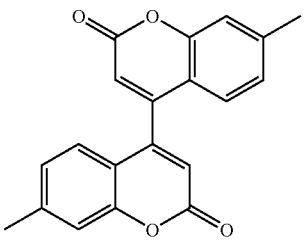

¹H NMR (300 MHz, CDCl₃) δ: 7.43(d, Ph, J=8.4 Hz, 1H), 7.37(d, Ph, J=8.4 Hz, 1H), 6.98(s, Ph, 1H), 6.44(s, CH, 1H), 2.31(s, CH3, 3H) ppm;

EI-MS (m/z, %): 318(M⁺, 38.85), 291(21.48), 290(100), 275(32.52), 273(67.88), 262(19.23), 261(19.01), 246(26.38);

IR (KBr, cm⁻¹):1973, 1724, 1613, 1573, 1560, 1489, 1418, 1180, 1130, 935, 814;

HRMS. $C_{20}H_{14}O_4$: calculated value 318.08921. measured value: 318.08975.

EXAMPLE 12

Preparation of 4,4'-di(6-fluoro) coumarin (12)

The yield was 22%.

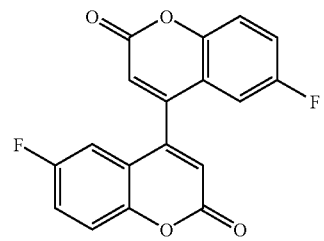

¹H NMR (300 MHz, d-DMSO) δ: 7.86(d, Ph, J=7.5 Hz, 1H), 7.55(s, Ph, 1H), 7.09(d, Ph, J=8.1 Hz, 1H), 5.95(s, CH, 1H) ppm;

EI-MS (m/z, %): 329(M⁺+3, 19.83), 328(M⁺+2, 100), 326(M⁺, 14.10), 310 (17.48), 299(16.14), 298(13.89), 258 (13.10), 257(50.74);

IR (KBr, cm$^{-1}$): 3053, 2925, 1766, 1721, 1568, 1485, 1430, 1263, 1226, 1189, 1170, 942, 926, 820;

HRMS. $C_{24}H_6F_2O_4$, calculated value: 326.03906. measured value: 326.03667.

EXAMPLE 13

Preparation of 4,4'-di(7-methoxy) coumarin (13)

The yield was 55%.

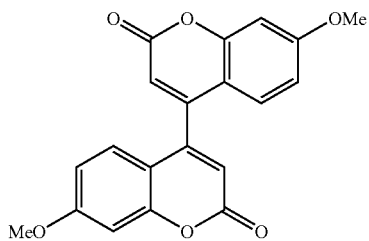

$^1$H NMR (300 MHz, CDCl$_3$) δ: 7.65(d, Ph, J=9.3 Hz, 1H), 7.38(d, Ph, J=8.1 Hz, 1H), 6.84(s, Ph, 1H), 6.27(s, CH, 1H), 3.88(s, OMe, 3H) ppm;

$^3$C NMR(300 MHz, CDCl$_3$) δ: 163.06, 161.55, 156.12, 143.74, 132.38, 132.25, 129.02, 128.85, 128.69, 113.30, 112.88, 112.76, 101.04, 56.03 ppm;

IR (KBr, cm$^{-1}$): 1721, 1706, 1614, 1558, 1506, 1465, 1400, 1353, 1284, 1234.

EXAMPLE 14

Preparation of 4,4'-di(7,8-phenyl) coumarin (14)

The yield was 63%.

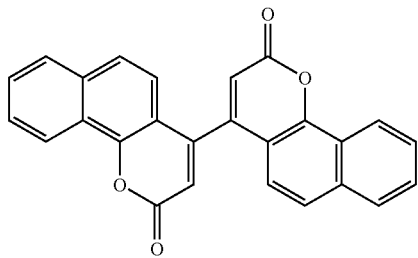

$^1$H NMR (300 MHz, CDCl$_3$) δ: 8.66(d, Ar, J=7.5 Hz, 1H), 7.89-7.57(m, Ar, 4H), 7.15(d, Ar, J=6.6 Hz, 1H), 6.62(s, CH, 1H) ppm;

EI-MS (m/z, %): 390(M$^+$, 69.95), 363(30.42), 362(100), 345(31.52), 318(30.22), 305(32.67), 276(37.38), 138(38.32);

IR (KBr, cm$^{-1}$): 1720, 1632, 1548, 1502, 1469, 1376, 1355, 1327.

EXAMPLE 15

Antifungal Activity of the Coumarin Compound of the Present Invention

Antifungal activity of one coumarin compound in the present invention, 4,4'-biisofraxidin having the formula of

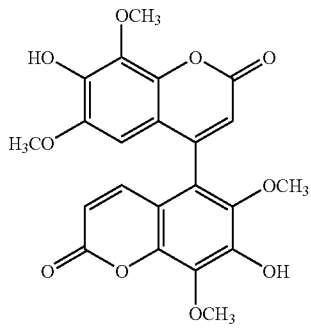

was tested by Jiangsu Hengrui Pharmaceutical Co., Ltd. The bioactivity against fungal infection of various antibiotics were tested. Some antibiotics such as Levofloxacin didn't show any significant bioactivity, while 4,4'-biisofraxidin of the present invention showed obvious antifungal activity to *Staphylococcus epidermidis* with minimal inhibitory concentration (MIC) value of 128 g/L towards comparatively sensitive strains. The compound also showed inhibitory effect on *candida Albicans* with a 10 mm inhibiting zone at the concentration of 10 μg/ml.

EXAMPLE 16

In Vivo Protective Test

Method

1. Preparation of Tested Fungus Liquor

2~3 monocolonies of selected tested fungus were inoculated in Sabouraud liquor culture medium, which was cultured for 18 hours at 37° C., and then it was diluted with 5% sterilized dried yeast liquor for next uses.

2. Test of Minimum Lethal Dose (MLD)

3. Healthy mice (lived in Kunming, China) weighed 18~22 g were divided into groups randomly with 5 mice in each group. The fungal liquor 0.5 ml was injected into a mouse, which was observed continuously for 7 days after infection. Mortality of the mice was recorded, and the minimum fungal dose that caused the mice be with a 100% mortality was named as MLD, which also was regarded as infection fungal dose in vivo protective test.

4. Preparation of Drug Liquor

All test drugs were confected to requested concentration with 0.5% CMC including Fluoroconazole and 4,4'-biisofraxidin.

5. Test Method of Infection and Treatment

Test mice were divided into groups randomly according to gender and weight, 5 males and 5 females in each group. The infection fungal liquor 0.5 ml was injected into each mouse at the abdominal region at 0.5 ml per mouse. Two hours prior to the infection and 4 hours after infection, mice were orally administered with Fluoroconazole or 4,4'-biisofraxidin by intragastric gavage at various concentration. The comparative group was tested at the same time. Mortality was recorded within 7 days after infection, and effective dosage at half (median effective dose, ED$_{50}$) and 95% confidence limit were calculated by the Bliss's method. Fluoroconazole and 4,4'-biisofraxidin were tested on their in vivo protection activity on *candida Albicans* 02-6 infected mice, and ED$_{50}$ was calculated by the Bliss's method at 95% confidence limit.

Results

The protective effect of Fluoroconazole and 4,4'-biisofraxidin on the mouse infected by *candida Albicans* were shown in Table 1.

TABLE 1

Protective Effect of Fluoroconazole and 4,4'-Biisofraxidin

| Infection Strain (Dose CFU*/ml) | Drug | Drug dose (mg/kg) | Mice | Survival | Survival rate (%) | $ED_{50}$ and 95% confidence limit (mg/kg) |
|---|---|---|---|---|---|---|
| candida Albicans 02-6 ($2.07 \times 10^4$) | Fluoroconazole | 200 | 10 | 8 | 80 | 135.89 (114.98–170.95) |
| | | 160 | 10 | 6 | 60 | |
| | | 128 | 10 | 4 | 40 | |
| | | 102.4 | 10 | 4 | 40 | |
| | | 89.2 | 10 | 2 | 20 | |
| | | 65.5 | 10 | 0 | 0 | |
| candida Albicans 02-6 ($2.07 \times 10^4$) | 4,4'-Biisofraxidin | 200 | 10 | 7 | 70 | 149.50 (127.97–130.7) |
| | | 160 | 10 | 6 | 60 | |
| | | 128 | 10 | 4 | 40 | |
| | | 102.4 | 10 | 3 | 20 | |
| | | 89.2 | 10 | 1 | 10 | |
| | | 65.5 | 10 | 0 | 0 | |
| Comparative Group | | — | 10 | 0 | 0.0 | |

*colony forming unit (CFU)

Conclusion 4,4'-Biisofraxidin had obvious protective effect by intragastric gavage on mice infected by *candida Albicans* 02-6 in vivo; the survival rate was 70% at a dosage of 200mg/kg. The in vivo protective effect of 4,4'-biisofraxidin was similar to that of Fluoroconazole on mice infected by *candida Albicans*.

EXAMPLE 17

In Vitro Drug Sensitivity MIC Test

Method

The tested fungi were confected to a suspension with normal saline, and further diluted to a suspension with the turbidity of more than 2.0 McFarland Standards (McF). Then, the suspension was diluted 100 times with normal saline, and diluted 10 times with RPMI1640, and the sample was diluted 2 times, which was cultured for 72 to 96 hours at a 96-well culture dish while being gently agitated and assayed for photoelectric colorimetric assay at 490 nm.

Tested fungi include *Saccharomyces*, *candida Albicans* 01-5, 01-1, 02-6, *candida Albicans* CMCC, *Aspergillus niger*, *Cryptococcus neoformans*, *Trichophyton rubrum*, and *Trichophyton verrucosum* and MIC Results were listed at Table 2.

TABLE 2

MIC Results of 4,4'-Biisofraxidin

| Strains Tested | Fluoroconazole (μg/ml) | 4,4'-Biisofraxidin (μg/ml) |
|---|---|---|
| Saccharomyces | 64 | >128 |
| candida Albicans | >128 | 64 |
| candida Albicans | >128 | >128 |
| candida Albicans 01-5 | 128 | 64 |
| candida Albicans CMCC | 64 | >128 |

TABLE 2-continued

MIC Results of 4,4'-Biisofraxidin

| Strains Tested | Fluoroconazole (μg/ml) | 4,4'-Biisofraxidin (μg/ml) |
|---|---|---|
| candida Albicans 02-6 | 64 | 32 |
| candida Albicans 01-1 | 128 | 64 |
| Aspergillus niger | >128 | 128 |
| Cryptococcus neoformans | 16 | 64 |
| Thichophyton rubrum | 16 | 16 |
| Trichophyton verrucosum | 128 | 128 |

Conclusion 4,4'-biisofraxidin had weak antifungal activity against *candida Albican* with an MIC value of 128 or above 128 μg/ml, and showed significant antifungal activity for *Aspergillus niger*, *Cryptococcus neoformans*, *Trichophyton rubrum*, and *Trichophyton verrucosum* with MIC values of 128, 64, 16, and 128 μg/ml, which antifungal activity was comparable to that of Fluoroconazole.

EXAMPLE 18

Bacteria Reverse Mutation Test

According to the conditions of mutation test in the Guide Compilation of New Medicament (Western Medicament) Before Clinic (Pharmacy, Pharmacology, and Toxicology) (Edition July 1993, Bureau of Pharmaceutical Policy, Chinese Department of Health), 4,4'-biisofraxidin was tested at a dosage of 5, 50, 500, 1000, and 5000 μg/dish in the system without $S_9$. It was found that 4,4'-biisofraxidin could inhibit the growth of bacteria *S. Typhimurium* TA97, TA98, TA 100, and TA102 at a high dose (5000 μg/dish), but no obvious effect at other four doses. Therefore, 4,4'-biisofraxidin was effective at high dosage for inhibiting bacteria growth, while it couldn't induce gene mutation for various strains of mice *Salmonella* at other dosages.

EXAMPLE 19

Chromosome Aberration Test of CHL Mammal Cell Induced by 4,4'-biisofraxidin

The purpose of the Example was to assess whether 4,4'-biisofraxidin caused the chromosome aberration of CHL cell. Firstly, Median Inhibitory Concentration ($IC_{50}$) was obtained by general method and regarded as the maximum dosage. Then, the maximum dosage was diluted at 0.5 time at multiple times to get three dosage groups. The experiment was conducted at a $—S_9$ system (without hamster liver $S_9$ system). $IC_{50}$ of 4,4'-biisofraxidin was determined to be 248 μg/ml, and the dosage was 62, 124, and 248 μg/ml. The antifungal compound was added to the cultured cell directly for 24 hours in order to observe whether 4,4'-biisofraxidin caused chromosome aberration in CHL cell. It was found that the mutagenicity of 4,4'-biisofraxidin was 12% at a high dosage (248 μg/ml) and 1% at low to medium dosage, and there was no correlation between the dosage and mutagenicity for all 3 test groups. Therefore, 4,4'-biisofraxidin was a weak mutagen at a relatively high dosage under the test conditions.

Considering the fact that 4,4'-biisofraxidin had antifungal activity, it was in accordance with its pharmacodynamics that the compound was effective at high dosage for inhibiting bacteria growth in the bacteria reverse mutation test while only showed low activity for induction as a weak mutagen of chromosome aberration test of CHL cell at a relatively high dosage.

EXAMPLE 20

Micronucleus Test of Mice Medulla

Seventy ICR mice were randomly divided into 7 groups with 10 mice per group having 5 males and 5 females in each group. The maximum tolerance dose (MTD) of the mice was more than 5000 mg/kg for 4,4'-biisofraxidin by intragastric gavage, so that the maximum dosage was 5000 mg/kg. Four dosage groups were set up with dosage amount of 5000, 2500, 1250, and 625 mg/kg, one negative and one positive control group. The intragastric gavage was carried out at once per day consecutively for 2 days. Samples were taken at 24 hours after the last intragastric administration and inspected under microscope. The observation showed that under the test conditions, 4,4'-biisofraxidin had no effect on inducing increase in micronucleus number in the mice medulla polychromatic erythrocyte micronucleus test. Therefore, 4,4'-biisofraxidin demonstrated a relatively low toxicity. Since there was no significant difference in comparison between different dosage groups with the negative group in the medulla polychromatic erythrocyte micronucleus test, it demonstrated that 4,4'-biisofraxidin was a safe compound.

EXAMPLE 21

Toxicity Test

Acute toxicity test in vivo of 4,4'-biisofraxidin in mice showed that half lethal dose ($LD_{50}$) was undetectable while the MTD was determined to be more than 5 g/kg (no death after testing 14 days in 14 mice). Thus, the toxicity was very low for the compound. Simultaneously, $LD_{50}$ of Fluoroconazole was about 1.6 g/kg (2 death after testing 14 days in 4 mice). Therefore, the toxicity of Fluoroconazole was three times larger than that of 4,4'-biisofraxidin. As a conclusion, 4,4'-biisofraxidin had high antifungal activity and low toxicity in comparison with Fluoroconazole.

EXAMPLE 22

Comparative Study on Liver Toxicity

This example evaluated liver toxicity of antifungal compound of the present invention, 4,4'-biisofraxidin, and Fluoconazole, and provided basis for further drug development.

Method and Result

1. Acute Toxicity Test

Acute toxicity of 4,4'-biisofraxidin and Fluoconazole were simultaneously evaluated and the toxicity reaction and mortality were observed and compared for values of LD50 for ICR mice which were orally administered with 4,4'-biisofraxidin or Fluoconazole.

ICR mice having a single dosage of 5 g/kg through oral administration showed no obvious toxicity reaction after 14 days of consecutive observation and no mortality (0/10). Thus, the MTD was higher than 5 g/kg.

ICR mice having a single dosage of Fluoconazole through oral administration appeared to be dispirited and inert, showed reduced physical activity, limbs seemed incapable of action, and 5 hours after administration, some individual mice showed signs of suffocation and died. The MTD was about 1.6 g/kg (2/4).

2. Comparison of Liver Toxicity

ICR mice were orally administered with 4,4'-biisofraxidin or Fluoconazole at the same dosage of 1.6 g/kg, and blood samples were taken at 4 hours and 24 hours after the administration, and serum was separated from blood samples for testing liver indices of asparate aminotransferase test (AST) and alanine aminotransferase test (ALT).

The serum level of ALT and AST of the ICR mice in the 4,4'-biisofraxidin and Fluconazole group were compared at Table 3.

TABLE 3

Serum ALT/AST Activity of ICR Mice

| Group | Time after Treatment | ALT (U/L)* | AST (U/L)* |
|---|---|---|---|
| 4,4'-biisofraxidin 1.6 g/kg | 4 hours | 47.5 (48, 47) | 93.5 (96, 91) |
| Fluconazole 1.6 g/kg | 4 hours | 84.5 (87, 82) | 189.5 (155, 224) |
| 4,4'-biisofraxidin 1.6 g/kg | 24 hours | 55 (46, 64) | 86 (80, 92) |
| Fluconazole 1.6 g/kg | 24 hours | 53.5 (40, 67) | 99 (73, 125) |

*Note: under these 2 columns, the first data showed the mean value and the second data in parent thesis showed values of each sample.

As indicated in Table 3, ICR mice administered with 4,4'-biisofraxidin did not show any significant abnormality 4 hours after the intake. As for ICR mice administered with Fluconazole, 3 out of 4 mice showed signs of being dispirited and inert, showed reduced physical activity, limbs seemed incapable of action. Two of the mice were dissected and tested for serum ALT and AST level, and the results were both higher than those of the 4,4'-biisofraxidin group.

Twenty-four hours after administration, 1 of the remaining 2 mice in the Fluconazole group had relatively high AST level while the other mice did not have significantly increased ALT or AST level. ICR mice in the 4,4'-biisofraxidin group had no abnormal changes in serum ALT, AST level either 4 hours or 24 hours after the oral administration. Therefore, ICR mice showed no obvious liver toxicity at an oral dosage of 1.6 g/kg, while oral administration of Fluconazole at the same dosage showed liver toxicity and the liver toxicity remained even 4 hours after the administration of the drug.

We claim:
1. A 4-substituted coumarin compound having a formula of

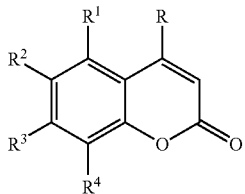

wherein R is a phenyl being substituted with —CHO or a naphthyl,
with $R^1$, $R^2$, $R^3$, and $R^4$ being H, an alkyl having $C_{1-10}$, X, $NO_2$, CN, $OCH_3$, $COOCH_3$ or $OR^5$, $R^5$ being H or an alkyl having $C_{1-10}$, and X being a halogen; and
wherein R is an aryl, the coumarin compound is not

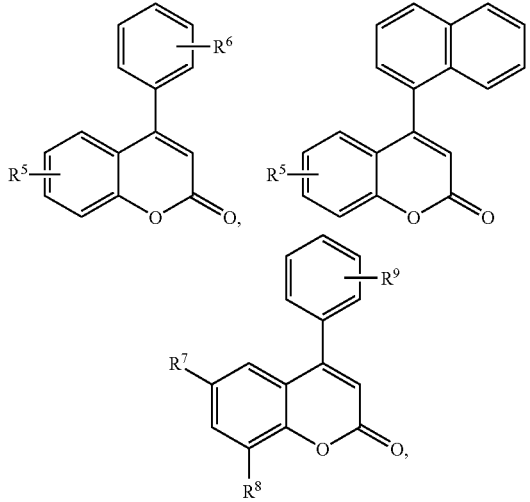

in which $R^5$ is H, OH, $OCH_3$, an alkyl having $C_{1-10}$, or a halogen; $R^6$ is H, $CH_3$, $CH_3O$ or a halogen; $R^7$ is $CH_3O$ or OH; $R^8$ is $CH_3O$ or OH; $R^9$ is H, $CH_3$, OH or —$OCH_2O$—.

2. The 4-substituted coumarin compound according to claim 1 further having one of the formulae:

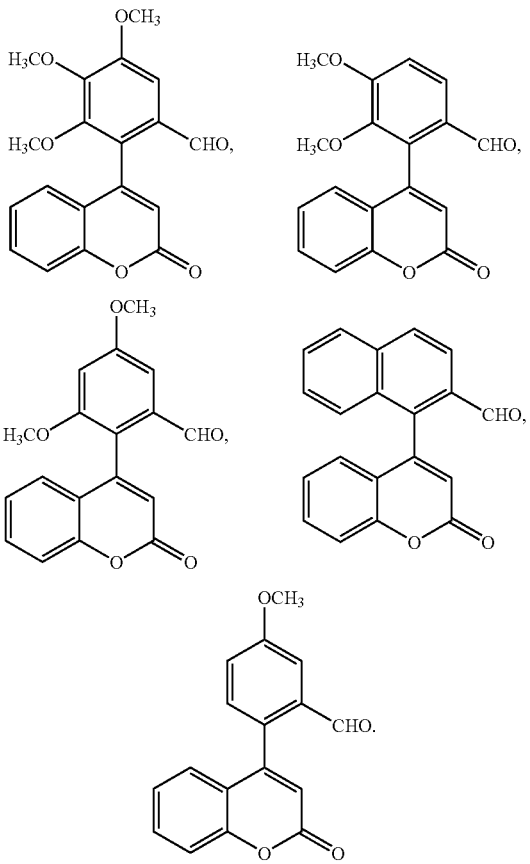

3. The 4-substituted coumarin compound of claim 1, wherein R is a phenyl group being substituted with —CHO and further mono- or poly-substituted with X, $NO_2$, an alkyl having $C_{1-10}$, —$OCH_2O$—, —$OCH_3$, —CN, or —$COOCH_3$.

* * * * *